United States Patent [19]

Patell

[11] Patent Number: 5,750,145

[45] Date of Patent: May 12, 1998

[54] STABLE GELATIN COATED ASPIRIN TABLETS

[75] Inventor: Mahesh Patell, Edison, N.J.

[73] Assignee: Bristol-Myers Squibb Company, New York, N.Y.

[21] Appl. No.: 508,647

[22] Filed: Jul. 28, 1995

[51] Int. Cl.$^6$ .............................. A61K 9/38; A61K 9/40; A61K 31/60

[52] U.S. Cl. .................. 424/478; 424/456; 424/463; 424/474; 424/477; 424/480; 514/970

[58] Field of Search ........................ 424/456, 463, 424/474, 478, 479, 480, 482, 477; 514/970

[56] References Cited

U.S. PATENT DOCUMENTS

| | | | |
|---|---|---|---|
| 650,760 | 5/1900 | Metcalf | 424/4.56 |
| 671,804 | 4/1901 | Metcalf | 424/478 |
| 1,879,762 | 9/1932 | Nitardy | 424/478 |
| 3,493,652 | 2/1970 | Hartman | 424/433 |

*Primary Examiner*—James M. Spear
*Attorney, Agent, or Firm*—Morton S. Simon

[57] ABSTRACT

Gelatin coated pharmaceutical dosage units containing, for example, analgesic compounds, such as aspirin, stabilized with a proteolytic enzyme, such as pepsin, are described.

10 Claims, No Drawings

STABLE GELATIN COATED ASPIRIN TABLETS

FIELD OF THE INVENTION

This invention pertains to stabilized pharmaceutical compositions, more particularly gelatin coated pharmaceutically active dosage units containing a therapeutically active ingredient which is subject to hydrolysis on storage as a result of moisture in the air or in one or more of the components of the dosage unit. It is especially concerned with the stabilization of analgesics such as gelatin coated aspirin tablets.

The stabilizing agent is a proteolytic enzyme. The presently preferred stabilizing agent is pepsin. This proteolytic enzyme has been found to be a useful stabilizing agent at remarkably low concentrations.

BACKGROUND OF THE INVENTION

Aspirin, or salicylic acid acetate is a well known therapeutic agent which has been employed for many years as an analgesic as well as for its antipyretic and anti-inflammatory properties.

Pepsin is a proteolytic enzyme which is the principal digestive enzyme of gastric juice. It controls the degradation of proteins to proteoses and peptones. Pepsin is obtained from hogs' stomachs by maceration in water acidulated with hydrochloric acid under frequent stirring for several days followed by salting out with sodium chloride or equivalent reagent. The pepsin is precipitated and floats to the surface from which it is recovered, purified and dried.

Pepsin is available as commercial preparations mixed with lactose. Such preparations have activities of from about 3000 to about 20,000 units. A pepsin preparation with an activity of 3000 digests not less than 3000 nor more than 3500 times its weight of coagulated egg albumin. As stated above, pepsin is the presently preferred proteolytic enzyme for use in this invention.

All of the available evidence leads to the conclusion that aspirin, which is a salicylic acid ester, becomes therapeutically active upon hydrolysis to form free salicylic acid (FSA). There are two principal problems with FSA. One is that it is very irritating to the gastric mucosa and is associated with dyspepsia and gastric bleeding. Accordingly, while the presence of salicylic acid in the stomach is desirable, efforts are made to retain the concentration of this agent at a low level.

A second problem with gelatin coated aspirin is that during storage FSA produced by moisture catalyzed hydrolysis of the aspirin denatures the gelatin making it insoluble in water. As a result, the therapeutic agent is not released. The principal source of moisture in gelatin coated products is in the gelatin film. The gelatin film which is enrobed on the tablet, initially contains approximately 30% moisture. When the gelatin film is dried, it contains approximately 6 to 8% moisture.

Much time and effort have been expended in attempts to stabilize aspirin and avoid the formation of FSA during the storage of aspirin dosage forms. The problem is multiplied many fold when aspirin dosage forms are stress tested by storage under high humidity and temperature conditions to meet expiration date requirements.

Early attempts to utilize silica or other water absorbents as water scavengers or to use solubilizing agents or disintegrating agents prior to applying a gelatin film on the tablet surface, proved fruitless since, on long storage, atmospheric moisture caused hydrolysis and formation of FSA. Other water scavengers, such as talcum powder, sodium lauryl sulfate, glycine, magnesium carbonate and the like, were similarly disappointing.

Subsequently, efforts were made to avoid hydrolysis by coating the aspirin with a thin layer of methyl cellulose or equivalent coating agent. These, too, were found to be of little value for stabilizing aspirin products against hydrolysis.

Next, attempts were made to improve stability by covering the methyl cellulose or equivalent coating with gelatin. The art often uses the term "enrobed" to describe this coating with gelatin. Although gelatin enhanced the appearance of the tablets and facilitated oral ingestion, it did not greatly improve stability because it retains water even under the most rigid drying conditions and is extremely hygroscopic. When gelatin coated aspirin tablets are stored, the retained and the absorbed water catalyze the formation of FSA.

Pepsin has been mentioned previously in connection with aspirin formulations. However, it has not been utilized to stabilize aspirin products in the same manner or, in fact, in any manner which is suggestive of the use described and claimed herein.

Metcalf in U.S. Pat. No. 650,760 and 671,804 describes the combination of pepsin and gelatin to assist in the digestion of the capsule shell or coatings of pills and tablets.

U.S. Pat. No. 1,879,762 mentions gelatin coated tablets which are protected against oxidative instability by incorporating an antioxidant such as hydroquinone in the coating.

U.S. Pat. No. 3,493,652 describes controlled release tablets in which the medicament is coated with an enzymatically hydrolyzable coating agent containing an enzyme which catalyzes the hydrolysis. Pepsin is specifically mentioned together with close to forty other hydrolytic enzymes.

U.S. Pat. No. 3,322,626 mentions compositions for the treatment of acne in which the therapeutic agent is mixed with pepsin or other hydrolytic enzyme. The tablet may be coated.

In U.S. Pat. No. 4,716,042, decomposition of aspirin in film coated aspirin tablets is said to be prevented by mixing the aspirin with citric, alginic or glutamic acid before coating. No mention is made of pepsin.

A desideratum of storage stability is passage of the two year test. Tests for achieving this result are described in USP XX on pages 56 et seq. the disclosure of which is incorporated herein. Aspirin preparations which pass these tests may be labeled as stable for a period of at least two years. This is the meaning of the term "stable" as used in the instant disclosure and claims. Aspirin preparations which test for not more than 3% FSA when stored at 40° C for 13 weeks or when stored at 35° C for 26 weeks at 75% relative humidity may be labeled "stable". Of course, products which are stored under ambient conditions for two years without formation of more than 3% FSA may also be labeled "stable".

BRIEF DESCRIPTION OF THE INVENTION

It has now, surprisingly, been discovered that very small amounts of pepsin are capable of stabilizing aspirin compositions against hydrolytic decomposition thus rendering these compositions "stable".

The aspirin dosage forms or units of this invention comprise a solid core containing a therapeutically effective amount of aspirin. There is a first protective coating on the core. This coating contains a quantity of pepsin which is effective to stabilize the aspirin for a period of 13 weeks at 40° C. and 75% relative humidity or for 26 weeks at 35° C. and 75% relative humidity. The coating comprises pepsin dispersed with a film forming polymer of the type commonly used in the trade for coating pharmaceutical preparations. The polymer is preferably, chemically inert, i.e., it does not react appreciably with any of the components of its environment including, for example aspirin, pepsin, gelatin, moisture or any of the fillers used in the preparations. Those skilled in the art will be well aware of such film forming materials.

The second coating on the dosage form is gelatin of the type normally employed for such purposes.

Although, for convenience this invention is described as applied to aspirin, it will be readily apparent to the skilled artisan that it is applicable to preserving the stability of other pharmaceuticals which are subject to degradation to produce acids or other products which denature gelatin. This would include active components which are acidic in nature or which produce acidic degradation products.

The products of the invention may contain, in addition to a therapeutically effective quantity of aspirin, at least one of a wide variety of other therapeutic components normally employed with aspirin. These include, for example, nasal decongestants (e.g. pseudoephedrine hydrochloride), antihistamines (e.g. chlorpheniramine maleate), sleep aids (e.g. diphenydramine dihydrogen citrate), analgesics (e.g. acetaminophen), antitussives (e.g. dextromethorpan hydrobromide), caffeine, or antacids such as magnesium oxide, calcium carbonate and the like. Acetaminophen and caffeine are especially preferred additives to aspirin compositions.

DETAILED DESCRIPTION OF THE INVENTION

Aspirin is well known. Some of its properties are briefly described above. A therapeutically effective amount of aspirin for the dosage forms of this invention will vary with the proposed utility and with the regimen for administration. The process of administration is oral, but a treatment dosage unit may be administered as one dosage unit, or as several dosage units over a period of time. Accordingly, the amount of aspirin in specific dosage units is not critical. Therapeutically effective amounts may vary over a wide range, typically from about 80 to about 700 milligrams per coated tablet or other dosage unit.

Pepsin, its properties, activities and the fact that it is available at a variety of activity levels has been described above.

The presently preferred film former for the first coat is Methocel or methyl cellulose. Other typically useful pharmaceutically acceptable film formers are hydroxy propyl cellulose, hydroxy propyl methyl cellulose, carboxy methyl cellulose, sodium carboxy methyl cellulose, polyvinyl pyrrolidone, methacrylic ethers (Eudragit available from Rhom Pharma), ethyl cellulose, methyl cellulose and pseudo latex Ethocel systems (available from FMC). Other useful materials will be known to the skilled artisan or can be identified by reference to *Remington's Pharmaceutical Sciences*, 18th Edition.

Gelatin is a well known coating material used in pharmaceutical practice. It is derived by acid or basic hydrolysis from the collagen of skin, tendons, ligaments and bones. It is available commercially in many forms. The principal commercial forms are acid bone gelatin and lime bone gelatin. These are presently preferred because of their ready availability. However, any pharmaceutically acceptable gelatin suitable for human administration may be employed in the invention. All forms of gelatin are water soluble, hygroscopic proteins. Their water content varies appreciably. When first layered on a tablet substrate, they are in the form of a flexible sheet with a water content of about 30% by weight based on the weight of the gelatin on a wet basis. When dried for commercial distribution of the tablets, the water content is about 6% by weight on the same basis.

While aspirin is normally the principal therapeutically active ingredient in the compositions of this invention, other therapeutic components such as those identified above may be employed in the mixture. Additionally the composition may contain other inert ingredients often employed in such compositions including disintegrants such as corn starch, cellulose (e.g., microcrystalline cellulose), Primogel, AC-DI-SOL, sodium carboxymethyl cellulose, Veegum HV, bentonite and others well known to the skilled artisan; lubricants such as magnesium, zinc or calcium stearates, stearic acid, mineral oil, waxes or sodium lauryl sulfate; fillers such as lactose, dicalcium phosphate, calcium sulfate, mannitol, kaolin, starch, etc; and buffering agents, typically magnesium, sodium or calcium carbonates.

The products of this invention can be produced by conventional procedures well known to those skilled in the art. The solid core may be produced, for example by compression on a tablet press. The first coating is typically applied by spray coating an aqueous solution or suspension containing the pepsin and film coating agent and, optionally, a plasticizer, while the cores are tumbled in a coating pan. The coating process is carried out at an elevated temperature so that the water contained in the coating solution or suspension flashes off when the solution or suspension is sprayed onto the tumbled cores.

The presently preferred procedure for forming the gelatin coating is the enrobing procedure described in U.S. Pat. No. 5,146,730, the entire disclosure of which is incorporated herein by reference. Briefly, the tablet is enrobed in a gelatin coating formed by application of respective layers of elastic gelatin film to opposite sides of the coated inner core. The applied gelatin layers conform tightly to the tablet surface, bond securely thereto and are sealed together in an essentially edge to edge manner at a seal line which extends around the tablet. Other equivalent procedures are known and can be employed.

As indicated above, pepsin preparations are available at a variety of activity levels. The amount of aspirin in the core may vary over a wide range. Accordingly, the amounts of each component in the final composition may vary appreciably. The principal variant is the pepsin. Generally, the minimum amount of pepsin to achieve stability will be employed. If the amounts of all of the other ingredients are kept essentially constant, the desired stability can be obtained by varying the amount of pepsin having a specific activity level or by varying the activity level of a specific amount of pepsin employed.

As will be apparent, the amount of pepsin which will be effective to achieve stabilization will vary with the activity of the pepsin selected and with the amount of aspirin to be stabilized. The optimum quantity of pepsin of a selected activity to achieve stabilization of dosage units containing a therapeutically effective amount of aspirin can be readily ascertained by a few simple tests or by calculation based on the teachings of this disclosure, especially the following description for the optimum amounts of pepsin in a gelatin coated tablet containing 674 mg of aspirin. If the inner core weighs more or less than 674 mg, the amount of pepsin utilized for stabilization will vary accordingly while maintaining the same weight ratios of the various components.

When the dosage unit contains an aspirin core which weighs 674 mg, the amount of pepsin having an activity of 3000 will be from about 0.2% to about 0.3% by weight.

Such coated tablets are then enrobed in gelatin using for example, the enrobing process of U.S. Pat. No. 5,146,730. The total amount of gelatin normally applied is from about 90 to 150 mg. per tablet, the average weight being about 114 mg. per tablet including the moisture content. The tablets therefore are coated with from about 11% to about 20% gelatin. Each of 100 tablets will contain about 0.2% to about 0.3% pepsin.

All weight percents are based on the total weight of the dosage unit, i.e., the core, the initial coating, the gelatin coating and any components in the said coatings.

A typical tablet of the invention the central core of which weighs about 674 mg and contains principally aspirin, may be coated with 5.055 mg of a mixture containing 2.5275 mg of pepsin and 5.5275 mg of methocel.

Other tablets in which the core weight is more or less than 674 mg., or the pepsin is of more or less activity, will contain different but equivalent amounts of the stated ingredients the exact amounts of which can be readily calculated by the skilled artisan following the teachings of this disclosure.

The following non-limiting examples are given by way of illustration only.

EXAMPLE 1

This example shows the efficacy of pepsin for the stabilization of aspirin.

Mixtures were prepared containing the components shown in the following table and reacted for 22 hours at 40° C. Aspirin was quantified by HPLC.

| Sample Composition Aspirin/Pepsin/Gelatin/Water (% Weight/Weight) | Aspirin Recovered (Potency after 22 hours at 40° C. (% of Initial) |
| --- | --- |
| 26/26/26/22 | 86.0 |
| 36/0/36/28 | 62.6 |

It will be observed that the amount of aspirin recovered in the composition protected with pepsin was appreciably higher than in the unprotected mixture, indicating that a larger amount of aspirin was hydrolyzed to FSA in the latter mixture.

EXAMPLE 2

Tablets were prepared by coating an inner solid core of aspirin using an aqueous mixture containing 7.5% pepsin and 7.5% Methocel. The amount of dried coating on the core was 0.75%. The tablet was then enrobed in gelatin to provide a final tablet weighing about 795 mg coated with 15% gelatin.

The tablets were then packaged in groups of 20 and 40 tablets, each package containing one standard dessicant. The aspirin tablets were then subjected to accelerated stability tests under the conditions shown in the following table. At selected intervals the tablets were tested to determine the amount of FSA formed. The stabilizing action of pepsin is readily apparent from the table. These tablets could be labeled as stable for two years.

| Condition | Interval | 20 Tablets per Package | 40 Tablets per Package |
| --- | --- | --- | --- |
| 40° C./75% | 4 weeks | 0.7 | 0.7 |
| Relative Humidity | 8 weeks | 1.3 | 1.9 |
|  | 13 weeks | 1.8 | 2.5 |
| 35° C./75% | 4 weeks | 0.6 | 0.7 |
| Relative Humidity | 8 weeks | 0.5 | 1.2 |
|  | 13 weeks | 0.9 | 1.7 |
|  | 20 weeks | 2.1 | 2.8 |
|  | 26 weeks | 2.6 | 3.0 |

What is claimed is:

1. An aspirin dosage unit comprising:

a: a solid core containing a therapeutically effective amount of aspirin;

b: a first coating on said core comprising a pharmaceutically acceptable film forming polymer and an amount of pepsin which is effective to stabilize the aspirin for a period of at least 13 weeks when the dosage unit is stored at 40° C. and 75% relative humidity or 26 weeks when it is stored at 35° C. and 75% relative humidity; and c: a gelatin coating enrobing said first coating.

2. The dosage unit of claim 1 in which the pepsin has an activity of from about 3000 to about 20,000 units.

3. The dosage unit of claim 1 in which the pepsin has an activity of about 3000 units.

4. The dosage unit of claim 1 in which the film forming polymer is methyl cellulose.

5. The dosage unit of claim 1 in which the core contains from about 80 to about 700 milligrams of aspirin.

6. The dosage unit of claim 1 in which the core contains aspirin together with at least one other therapeutic agent.

7. The dosage unit of claim 6 in which the therapeutic agent is selected from the group consisting of nasal decongestants, antihistamines, sleep aids, analgesics, antitussives, antacids and caffeine.

8. The dosage unit of claim 6 in which the therapeutic agent is acetaminophen or caffeine.

9. A method for stabilizing an aspirin dosage unit so that aspirin contained therein is stable for a period of at least 13 weeks when the dosage unit is stored at 40° C. and 75% relative humidity or 26 weeks when it is stored at 35° C. and 75% relative humidity; said dosage unit comprising a solid core containing a therapeutically effective amount of aspirin, a first coating on the core comprising a pharmaceutically acceptable film polymer, and a gelatin coating enrobing the first coating, said method comprising also coating the core with an amount of pepsin effective to stabilize the aspirin for said period.

10. The method of claim 9 wherein the pepsin is incorporated in the first coating.

* * * * *